United States Patent [19]
Kristall et al.

[11] Patent Number: 5,374,281
[45] Date of Patent: * Dec. 20, 1994

[54] HYSTERESIS IN A RATE-RESPONSIVE PACEMAKER

[75] Inventors: Raymond A. Kristall, Dallas, Tex.; James L. Duncan, Alpharetta, Ga.

[73] Assignee: Siemens Pacesetter, Inc., Sylmar, Calif.

[*] Notice: The portion of the term of this patent subsequent to Aug. 24, 2010 has been disclaimed.

[21] Appl. No.: 15,714

[22] Filed: Feb. 9, 1993

[51] Int. Cl.$^5$ ............................................. A61N 1/362
[52] U.S. Cl. ..................................................... 607/17
[58] Field of Search .................... 607/7, 13, 15, 16, 17, 607/18

[56] References Cited

U.S. PATENT DOCUMENTS

| | | | |
|---|---|---|---|
| 4,562,841 | 1/1986 | Brockway et al. | 128/419 |
| 4,590,944 | 5/1986 | Mann et al. | 128/419 |
| 4,712,555 | 12/1987 | Thornander et al. | 128/419 |
| 4,719,920 | 1/1988 | Alt et al. | 128/419 |
| 4,788,980 | 12/1988 | Mann et al. | 128/419 |
| 4,790,318 | 12/1988 | Elmqvist et al. | 128/419 |
| 4,803,987 | 2/1989 | Calfee et al. | 128/419 |
| 4,813,421 | 3/1989 | Baudino et al. | 128/633 |
| 4,856,523 | 8/1989 | Sholder et al. | 128/419 |
| 4,940,052 | 7/1990 | Mann et al. | 128/419 |
| 4,944,298 | 7/1990 | Sholder | 128/419 |
| 5,040,534 | 8/1991 | Mann et al. | 128/419 |
| 5,040,535 | 8/1991 | Mann et al. | 128/419 |
| 5,237,992 | 8/1993 | Poore | 607/18 |

Primary Examiner—William E. Kamm
Assistant Examiner—George Manuel
Attorney, Agent, or Firm—Malcolm J. Romano

[57] ABSTRACT

A rate-responsive pacemaker includes programmable hysteresis means for automatically extending an escape interval, $EI_0$, in the presence of sensed intrinsic cardiac activity, and returning the escape interval to its initial value in the presence of pacemaker-stimulated (paced) cardiac activity. The escape interval sets the rate at which stimulation pulses are generated on demand in the absence of sensed intrinsic cardiac activity. The initial value of the escape interval is selected to be the lessor of: (a) a programmed escape interval (determined from a minimum programmed rate), or (b) a sensor-indicated escape interval (determined from a physiological or metabolic sensor used as part of the rate-responsive pacemaker). In addition to the hysteresis mode, a scan mode is optionally provided wherein the escape interval, $EI_0$, is gradually extended (lengthened) in small incremental steps if no intrinsic activity is sensed during the prior escape interval. In this manner, the pacemaker incrementally "scans" through an increasingly longer window of time looking for the occurrence of intrinsic cardiac activity before generating a stimulation pulse. A hysteresis rate adjust (HRA) mode is also optionally provided wherein the escape interval is gradually returned to $EI_0$ over several pacing cycles, rather than abruptly returning to $EI_0$ in a single step after the hysteresis mode has been ended due to no sensed intrinsic activity during the hysteresis escape interval $EI_H$.

20 Claims, 6 Drawing Sheets

HYSTERESIS IN A RATE-RESPONSIVE PACEMAKER

BACKGROUND OF THE INVENTION

FIELD OF THE INVENTION

The present invention relates to implantable medical devices and methods, and more particularly, to the use of hysteresis within a rate-responsive pacemaker.

A pacemaker is an electronic device, usually implanted, that generates electrical stimulation pulses that are delivered to the heart of a patient in order to cause the patient's heart to contract, or beat, at a prescribed rate. For example, if it is desired that the heart rate of the patient be maintained at 70 beats per minute (bpm), then the pacemaker is set to generate stimulation pulses at a rate of 70 pulses per minute (ppm), with each stimulation pulse, causing the heart to beat (i.e., causing the cardiac muscle tissue to depolarize and contract).

Most modern pacemakers are programmable. That is, the rate at which stimulation pulses are generated, as well as numerous other operating parameters associated with the pacemaker, are parameters that may be selected, typically using noninvasive programming means by the patient's physician or other medical personnel. The operation and programmable features of modern implantable pacemakers are well known and described in the art. See, e.g., Furman et al. *A Practice of Cardiac Pacing*, Futura Publishing Company, Inc. (Mount Kisco, N.Y. 1986); Moses et al.; *A Practical Guide to Cardiac Pacing*, Little Brown and Company (Boston/Toronto 1983). See also, e.g., U.S. Pat. Nos. 4,712,555 (Thornander et al.); 4,788,980 (Mann et al.); 4,940,052 (Mann et al.); and 4,944,298 (Sholder), which patents are incorporated herein by reference.

In order to allow the patient's heart to beat "on its own," without the need for an external stimulation pulse generated by a pacemaker, it is common in the art to operate an implantable pacemaker in a demand mode of operation. In a demand mode, the pacemaker monitors the heart to determine if a cardiac contraction (heartbeat) has naturally occurred. Such natural (non-stimulated) contractions, also referred to as "intrinsic" or "sinus" cardiac activity, are manifest by the occurrence of recognizable electrical signals that accompany the depolarization or contraction of cardiac muscle tissue. (While the depolarization of cardiac muscle tissue is technically a separate event from the actual contraction of cardiac muscle tissue —with depolarization immediately preceding contraction—for most purposes, and certainly for purposes of the present application, depolarization and contraction may be considered as simultaneous events, and the terms "depolarization" and "contraction" are used herein as synonyms.) The depolarization of atrial muscle tissue, for example, is manifest by the occurrence of a signal known as the "P-wave." Similarly, the depolarization of ventricular muscle tissue is manifest by the occurrence of a signal known as the "R-wave." The sensing of signals representing the occurrence of P-waves and R-waves, and other related signals, comprise the electrocardiogram (ECG) of the patient when sensed external to the heart, e.g., at the skin. When these same signals are sensed internal to or on the heart, they are generally referred to as the electrogram (EGM) of the heart.

In a demand mode of operation, the pacemaker monitors the heart for the occurrence of P-waves and/or R-waves. If such signals are sensed within a prescribed time period or time window, typically referred to as an "escape interval," then the escape interval is reset (i.e., restarted) and no stimulation pulse is generated. The escape interval is measured from the last heartbeat, i.e., from the last occurrence of a P-wave (if the atrium is monitored), or R-wave (if the ventricle is monitored), or the generation of a stimulation pulse (if natural activity does not occur). If the escape interval "times-out," i.e., if a time period equal to the escape interval has elapsed without the sensing of a P-wave and/or R-wave (depending upon which chamber of the heart is being monitored), then a stimulation pulse is generated at the conclusion of the escape interval, and the escape interval is reset, i.e., restarted. In this way, the pacemaker provides stimulation pulses "on demand," i.e., only as needed, when intrinsic cardiac activity does not occur within the prescribed escape interval.

Hence, it is seen that it is the escape interval that defines the rate at which stimulation pulses are generated by the pacemaker. In a demand mode of operation, the pacemaker provides stimulation pulses, when needed, at the rate set by the escape interval, even through the natural or intrinsic rhythm of the heart may occur at a rate faster than the escape interval. For example, if it is desired that the heart rate never slow to a rate less than 60 bpm, then the escape interval is set to 1000 milliseconds (msec), or 1 second, corresponding to the period of a 1 Hz signal. So long as intrinsic cardiac activity occurs at a rate faster than 60 bpm, i.e., so long as less than 1000 msec occurs between natural heartbeats, then no stimulation pulse is generated. However, as soon as 1000 msec occurs since the last natural heartbeat, a stimulation pulse is generated. In this way, the heart is assured of beating at least once every 1000 msec.

One of the programmable modes that has been used with programmable pacemakers for many years is a mode known as the "hysteresis" mode. The hysteresis mode is used in conjunction with selected other modes, such as single-chamber demand pacing, to allow the natural sinus rhythm of the heart to persist at rates less than the programmed minimum rate of the pacemaker. The programmed minimum rate of the pacemaker, in turn, sets the pacemaker escape interval. During pacing, i.e., during those times when the pacemaker is generating stimulation pulses, the pacemaker thus stimulates the heart at the rate set by the escape interval, i.e., upon the timing-out of each escape interval. When the hysteresis mode is enabled, sensed cardiac activity causes the pacemaker escape interval to be extended, or lengthened, thereby providing a longer period of time within which natural cardiac activity may occur before the pacemaker steps in to generate a stimulation pulse. Should the intrinsic rate of the heart fall below the programmed hysteresis rate, i.e., should no intrinsic cardiac activity be sensed during the lengthened escape interval, then a stimulation pulse is generated, and the escape interval reverts back to its initial value, as determined by the programmed minimum rate.

As an example of the hysteresis mode of operation, assume that the programmed minimum rate of a pacemaker is 70 ppm, corresponding to an escape interval of 857 msec. Further, assume that the programmed hysteresis rate is 50 ppm, corresponding to an extended escape interval of 1200 msec. At these values, the pacemaker maintains a minimum heart rate of 70 bpm, providing a stimulation pulse every 857 msec. Upon the occurrence of intrinsic cardiac activity, the escape interval is extended 350 msec, making the total extended escape interval equal to 1200 msec. So long as intrinsic cardiac activity continues to be sensed during this extended escape interval, i.e., so long as the natural sinus rhythm does not slow to a rate less than 50 bpm, then no stimulation pulses are generated. However, as soon as the extended escape interval times-out without the occurrence of natural cardiac activity, i.e., as soon as the natural sinus rhythm drops to a rate less than 50 bpm, then a stimulation pulse is generated and the escape interval is shortened back to its original value, i.e., back to 857 msec. The next stimulation pulse, and all subsequent stimulation pulses, occur at the programmed minimum rate, 70 ppm, unless interrupted by a sensed natural cardiac activity as described above.

The hysteresis mode of operation advantageously serves a dual purpose. First, it allows the patient's heart to beat at its own rhythm more often. Second, it prolongs pacemaker longevity. Pacemaker longevity is determined by the limited energy stored within the pacemaker. Such energy is stored in a battery. Most of the power drained from the battery is caused by the generation of stimulation pulses. Hence, the frequency with which stimulation pulses are generated has a profound effect upon pacemaker longevity. Advantageously, the hysteresis mode reduces the frequency at which stimulation pulses must be generated for most patients. Hence, the longevity of the pacemaker is increased when a hysteresis mode is invoked.

Disadvantageously, the hysteresis mode is not typically available for certain pacemaker modes of operation. For example, in dual-chamber pacing, such as operation in a DDD mode of operation (see, e.g., U.S. Pat. No. 4,944,298 (Sholder) for an explanation of the various pacemaker modes, and the three- or four-letter code used to identify such modes) hysteresis has not generally been used. This is because the whole idea behind DDD pacing is to allow the heart to be paced at a rate set by the sino-atrial (SA) node, thereby providing a true physiologic pacing regime with the maintenance of AV synchrony.

In atrial-based DDD pacing, all timing is controlled from the sensing of atrial activity (a P-wave). When a P-wave is sensed, two separate timers are started that operate in parallel. A first timer defines an atrial escape interval which, if timed-out, results in an atrial paced event. A second timer defines a separate AV delay which, if timed-out, results in a ventricular paced event. The first and second timers both start upon sensing atrial activity. The AV delay timer does not affect the basic atrial escape interval timer. The atrial escape interval timer thus controls the basic functioning rate of the pacemaker from atrial to atrial event. The ventricle is paced, if needed, at a rate that tracks the sensed atrial rate. If no atrial activity is sensed, then the atrium is also paced at a rate equal to the minimum set rate. Any reduction in the atrial paced rate below the minimum rate, such as might be introduced by hysteresis, has heretofore been viewed as not necessary, and has not been pursued. Nonetheless, even when operating in such atrial-based mode, there still remains a need to enhance pacemaker longevity, as well as a need to allow the heart to beat at its own rhythm more often. Such needs could best be met by providing a hysteresis mode of operation for atrial-based DDD pacing.

In addition to above-described atrial-based DDD pacing, there is also a second type of DDD operation known as ventricular-based DDD pacing. In ventricular-based DDD pacing (sometimes referred to as ventricular-based timing), two sequential timers are used. After an atrial event, an AV Delay timer is started. There is no coincident starting of a basic escape interval timer as occurs in the atrial-based DDD pacing. If the AV Delay timer times-out all the way, a ventricular pulse (V-pulse) is provided. If an R-wave is sensed before the AV Delay timer times-out, such sensing terminates the AV Delay timer. The sensing of an R-wave or the generating of a V-pulse thus comprise a ventricular event. After a ventricular event, an Atrial Escape Interval timer begins. If this Atrial Escape Interval timer times-out all the way, an atrial pulse (A-pulse) is provided. If a P-wave is sensed before the Atrial Escape Interval timer times-out, such sensing terminates the Atrial Escape Interval Timer. The sensing of a P-wave or the generating of an A-pulse thus comprise an atrial event, which atrial event again starts the AV Delay timer. Thus, in this way, the two timers of a ventricular-based DDD pacing system, function sequentially as opposed to the concurrent or parallel function of the timers in the atrial-based DDD pacing system. However, as with the atrial-based DDD pacing system, a ventricular-based DDD pacing system also faces a need to enhance pacemaker longevity, as well as a need to allow the heart to beat at its own rhythm more often. Such needs could best be met by providing a hysteresis mode of operation for ventricular-based DDD pacing.

Further, the hysteresis mode has not heretofore been used with rate-responsive pacing. In a rate-responsive pacer (note that the terms "pacer" and "pacemaker" are used herein as synonyms), some sort of physiological sensor is used to sense and measure a physiological parameter indicative of how fast the heart should be paced by the pacemaker (the "sensor-indicated rate"). For example, during periods of high physical activity, e.g., exercise, it is desirable that the heart be paced at a faster rate. To this end, a rate-responsive pacer senses such physical activity and adjusts the escape interval of the pacer accordingly so that the pacer's stimulation pulses are provided on demand at a faster rate during periods of sensed high physical activity (or other sensed physiological indicators). Hysteresis has not heretofore been used with rate-responsive pacers because the escape interval of such pacers is already changing as a function of the sensor-indicated rate, and any variations of the escape interval beyond those indicated by the pacer's physiological sensor have been viewed as undesirable and disruptive to the sensed physiologic pacing rate. Nonetheless, even when operating in a rate-responsive mode, there still remains a need to enhance pacemaker longevity, as well as a need to allow the heart to beat at its own rhythm more often. There is thus a need in the art for some type of hysteresis mode that can be used with a rate-responsive pacer.

SUMMARY OF THE INVENTION

The present invention addresses the above and other needs by providing a hysteresis mode for use with a rate-responsive and/or dual-chamber pacemaker, regardless of whether such pacemaker operates in an atrial-based timing mode or a ventricular-based timing mode. Such hysteresis mode advantageously allows a patient's heart to beat at its own natural rhythm more often, even when the pacer is operating in a rate-responsive, atrial-based, or ventricular-based timing mode, thereby reducing the number of stimulation pulses that must be generated by the pacemaker, and thereby also prolonging the life of the pacemaker.

A rate-responsive pacemaker that implements the hysteresis mode of the present invention includes the following elements: (1) first sensing means for sensing intrinsic cardiac activity; (2) second sensing means for sensing a physiologic or metabolic parameter indicative of the rate at which the heart should beat (a "sensor-indicated rate"); (3) a pulse generator that generates stimulation pulses; and (4) control means for defining a base escape interval, $EI_0$, that sets the rate at which the pulse generator generates stimulation pulses on demand, i.e., in the absence of sensed intrinsic cardiac activity. In accordance with conventional rate-responsive operation, the basic escape interval is selected to be the greater of: (a) a programmed escape interval (determined from the minimum programmed rate), or (b) a sensor-indicated escape interval (determined from the sensor-indicated rate).

The hysteresis mode of the present invention may advantageously be selectively programmed ON or OFF. When ON, the first sensing means of the pacemaker determines whether any intrinsic cardiac activity has occurred during the base escape interval, $EI_0$. If not, a stimulation pulse is generated at a rate determined by the base escape interval. If so, the basic escape interval is adjusted by a specified amount, effectively extending the base escape interval, $EI_0$, to an extended value, $EI_H$. The extended value of the escape interval, $EI_H$, is thereafter used by the pacemaker as the pacemaker's escape interval as long as the first sensing means senses intrinsic cardiac activity during the escape interval, $EI_H$. However, should no intrinsic cardiac activity be sensed during the extended escape interval $EI_H$, then a stimulation pulse is generated, and the value of the escape interval used thereafter by the pacemaker is returned to the basic escape interval, $EI_0$.

When operating in a DDD mode of operation, the base escape interval, $EI_0$, or the extended escape interval, $EI_H$, are typically defined by controlling the time interval defined by the atrial escape interval timer that starts with the occurrence of an atrial event (when using atrial-based timing) or the time interval defined by the atrial escape interval timer that starts with the occurrence of a ventricular event (when using ventricular-based timing). However, it is to be recognized that when ventricular-based timing is used during DDD operation, the base escape interval, $EI_0$, as well as the extended escape interval, $EI_H$, may also be defined by controlling both the atrial escape interval set by the atrial escape interval timer, as well as the AV Delay, set by the AV Delay timer. This is because the overall pacing rate set by a DDD pacemaker operating using ventricular-based timing is determined by the sum of the atrial escape interval and the AV Delay.

In addition to the hysteresis mode as described above, the present invention advantageously offers two additional modes that may be optionally used in conjunction with the hysteresis mode. A first additional mode is a scan mode wherein the base escape interval, $EI_0$ (which is normally derived from the sensor-indicated rate), is gradually extended (lengthened) in small incremental steps when no intrinsic activity is sensed during the prior escape interval. Such incremental extending of the base escape interval continues after each delivered stimulation pulse until the escape interval has been extended a maximum amount, typically to the hysteresis escape interval, $EI_H$. Thus, the pacemaker incrementally "scans" through an increasingly longer window of time looking for the occurrence of intrinsic cardiac activity before a stimulation pulse is generated.

A second additional mode of the present invention is a hysteresis rate adjust (HRA) mode. The HRA mode is invoked, when programmed ON, whenever a stimulation pulse has been generated at the conclusion of the hysteresis escape interval, $EI_H$. The generation of a stimulation pulse at the timing-out of $EI_H$ normally signals the termination of the hysteresis mode. When the HRA mode is programmed ON, however, the hysteresis mode is not abruptly ended by returning the escape interval back to $EI_0$ in a single step, as is common in prior art pacemakers that utilize hysteresis. Rather, the escape interval is gradually returned to $EI_0$ over several pacing cycles. Should intrinsic cardiac activity be detected as this transition from $EI_H$ to $EI_0$ is taking place, however, the escape interval returns to $EI_H$. In this manner, the rate-responsive pacemaker eases out of the hysteresis mode back to the normal rate-responsive mode.

One embodiment of the present invention may be characterized as a rate-responsive pacemaker that includes: (1) pacemaker means for sensing cardiac activity and for generating a pacing pulse at a rate set by a rate control signal in the absence of sensed cardiac activity; (2) means for generating a programmed rate signal; (3) sensor means for generating a sensor signal, the sensor signal varying as a function of sensed physiological and/or metabolic need; (4) means for generating a sensor-indicated rate (SIR) signal as a function of the sensor signal; (5) selection means for selecting one of the programmed rate signal or the SIR signal as the rate control signal for the pacemaker; and (6) hysteresis means within the pacemaker for adjusting the rate control signal upon sensing cardiac activity so that sensed cardiac activity can occur at a rate that is slower than the rate at which pacing pulses can occur.

Another embodiment of the invention is also directed to a rate-responsive pacemaker, and may be characterized as including: (1) sensor means for sensing a physiological or metabolical parameter and providing a sensor-indicated rate (SIR) signal indicative of the physiological or metabolical parameter; (2) timing means for generating an escape interval having a normal duration that varies as a function of the SIR signal; (3) pacing means for generating a stimulation pulse upon the timing-out of the escape interval; (4) reset means for resetting the escape interval upon the occurrence of intrinsic cardiac activity; and (5) hysteresis means for extending the escape interval to an extended duration upon the occurrence of intrinsic cardiac activity, and returning the escape interval to its normal duration upon the generation of a stimulation pulse. With such embodiment, intrinsic cardiac activity may occur at a rate that is slower than the rate at which stimulation pulses are generated even when the rate at which stimulation pulses are generated varies as a function of the SIR signal.

Yet a further embodiment of the invention may be characterized as a method of adjusting the escape interval (EI) of a rate-responsive (RR) pacemaker so that intrinsic cardiac activity may occur at a slower rate than paced cardiac activity. The pacemaker wherein such method is used includes means for sensing a physiological parameter, and timing means for establishing a base escape interval $EI_0$ having a duration that varies as a function of the sensed physiological parameter or a programmed pacing rate, whichever is shorter. The method includes the steps of:

(a) starting the timing-out of the escape interval $EI_0$;

(b) determining whether intrinsic cardiac activity occurs before the timing-out of the escape interval $EI_0$;

(c) generating a stimulation pulse in the event no intrinsic cardiac activity occurs as determined in step (b) and then repeating steps (a) and (b); and (d) initiating a hysteresis mode in the event intrinsic cardiac activity occurs as determined in step (b).

The initiating of the hysteresis mode in accordance with this method includes the steps of:

(1) increasing the escape interval to a new value, $EI_H$, where $EI_H = EI_0 + H$, and H is a factor derived from $EI_0$ in accordance with a prescribed relationship;

(2) starting the timing-out of the escape interval $EI_H$;

(3) determining whether intrinsic cardiac activity occurs before the timing-out of the escape interval $EI_H$;

(4) repeating steps (2) and (3) upon the occurrence of intrinsic cardiac activity as determined in step (3); and (5) generating a stimulation pulse upon the timing-out of the escape interval $EI_H$ without the occurrence of intrinsic cardiac activity as determined in step (3), resetting the escape interval to $EI_0$, and returning to step (a).

It is thus a feature of the present invention to provide a pacemaker that includes a hysteresis mode that may be programmably selected for use in rate-responsive pacing, and/or for use in dual-chamber pacing, such as DDD pacing, including DDD pacing based on atrial timing, and/or DDD pacing based on ventricular timing.

It is another feature of the invention to provide a rate-responsive pacemaker that selectively includes a hysteresis mode, whereby pacemaker longevity is enhanced and the heart is afforded the opportunity to beat at its own rhythm more often, even in the presence of a varying escape interval set by a physiologic sensor.

It is a further feature of the invention to provide a scan mode of operation for use in a rate-responsive or other pacer. It is a feature of the scan mode to gradually extend (lengthen) the basic escape interval of the pacer in small incremental steps if no intrinsic activity is sensed during the prior escape interval. In this manner, the pacemaker incrementally "scans" through an increasingly longer window of time looking for the occurrence of intrinsic cardiac activity before a stimulation pulse is generated.

It is an additional feature of the invention to provide a hysteresis rate adjust (HRA) mode of operation for use with a hysteresis mode of operation in a rate-responsive or other pacer. It is a feature of the HRA mode to gradually return the operation of the pacer from the hysteresis mode to the normal rate-responsive mode over several pacing cycles, rather than making this change in a single step. The HRA mode realizes this feature by gradually shortening the hysteresis mode escape interval over several paced cycles until the escape interval has been shortened to the pacer's base escape interval or SIR interval.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components or elements throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As described previously, it is noted that there are two types of pacemaker timing used with dual-chamber pacing modes, e.g., DDD pacing modes, whether providing rate-responsive functions or not. A first type of pacemaker timing is an atrial-based timing system, wherein ventricular pacing, if provided at all, follows an atrial event by a prescribed amount (the AV Delay interval amount). The basic pacemaker timing, including the base escape interval of the pacemaker, is thus keyed off of atrial events, i.e., the sensing of a P-wave or the providing of an A-pulse. A second type of pacemaker timing is a ventricular-based timing system, wherein ventricular pacing, if provided at all, follows the timing out of an AV Delay interval after an atrial event (P-wave or an A-pulse); and atrial pacing, if provided at all, follows the timing out of an Atrial Escape Interval following a ventricular event (R-wave or a V-pulse). The basic pacemaker timing is thus keyed off the sequence of atrial and ventricular events, with the Atrial Escape Interval usually being the parameter that is changed to vary the pacing rate, as it is by far the dominate parameter (in terms of length or duration) when compared to the AV Delay interval. For simplicity of explanation, the description of the timing adjustments provided by the present invention are described in terms of an atrial-based timing system. However, it is to be understood that such timing adjustments also have applicability to a ventricular-based timing system.

One embodiment of the present invention is intended for use with a rate-responsive pacemaker. A basic understanding of the operation of a rate-responsive pacemaker will thus be helpful. Accordingly, reference is first made to FIG. 1 where there is shown a functional block diagram of one embodiment of a rate-responsive pacer. This functional block diagram will be used to teach the basic operating principles of a rate-responsive pacemaker. A detailed description of a rate-responsive pacemaker may be found in the literature. See, e.g., U.S. Pat. No. 4,940,052 (Mann et al.).

Figure 1:
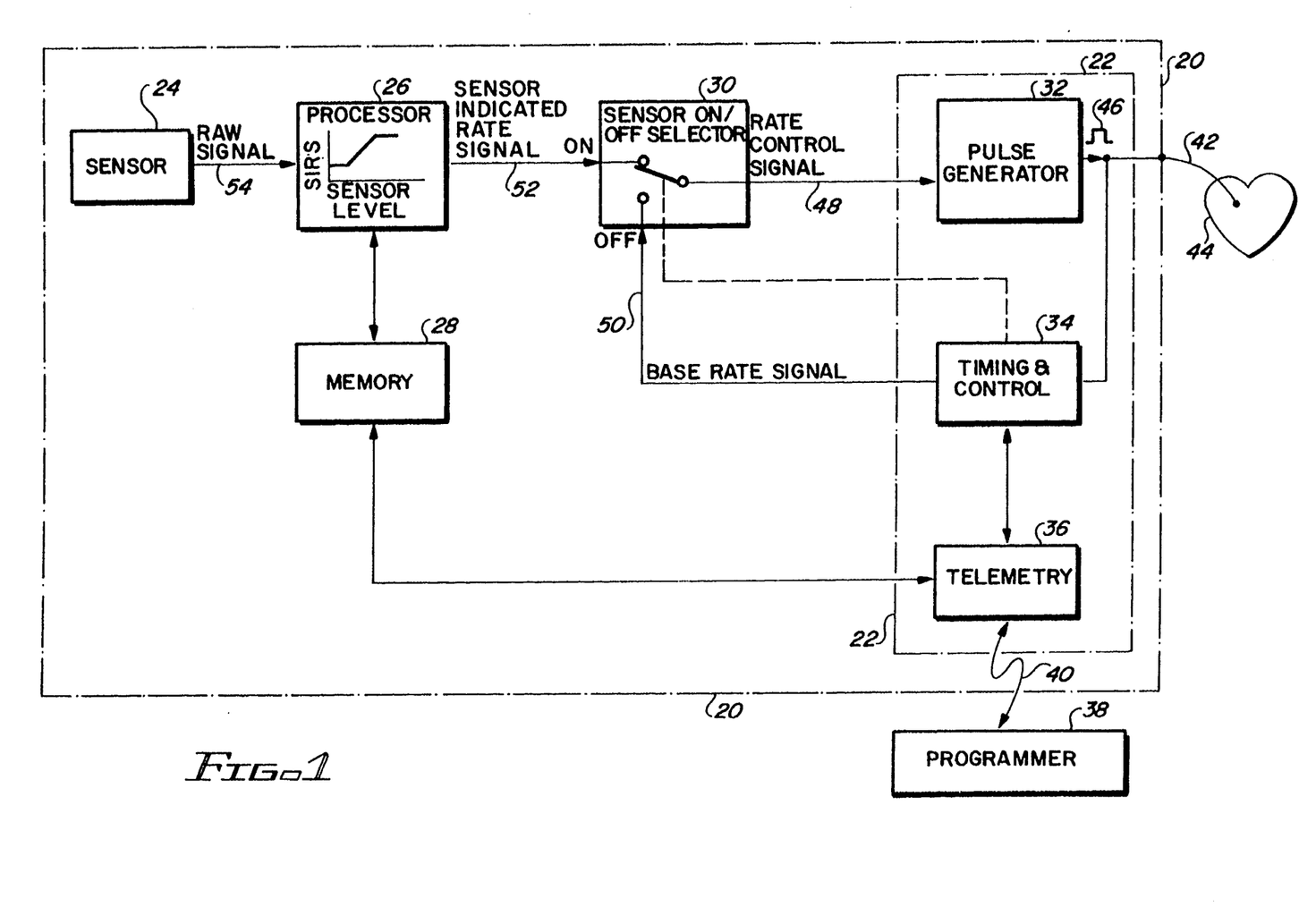
FIG. 1 shows a block diagram of a rate-responsive pacemaker.

Referring to the functional block diagram of FIG. 1, a representative rate-responsive pacemaker 20 is shown. The pacemaker 20 includes a conventional pacemaker chip 22, a sensor 24, a processor 26, memory circuit 28, and a selection means 30. The conventional pacemaker chip 22 includes at least a pulse generator 32, timing and control circuits 34, and telemetry circuits 36. The pulse generator 32 includes at least one lead 42 that provides an electrical contact with the patient's heart 44. An external programmer 38 is also used to send programming signals to the telemetry circuits 36. These programming signals are depicted symbolically as the wavy line 40 in FIG. 1. It is noted that such signals may be sent either from the programmer 38 to the pacemaker 20, or from the pacemaker 20 to the programmer 38.

Functionally, the pulse generator generates stimulation pulses 46 at a rate determined by a rate control signal, appearing on signal line 48. These pulses, in turn, are delivered to the heart 44 through the lead 42 in conventional manner. The lead 42 may be either a unipolar lead, bipolar lead, or other multi-pole lead as is known in the art. While the sensor 24 is shown in FIG. 1 as being included within the pacemaker 20, it is to be understood that the sensor 24 could also be included within, or coupled to, the lead 42; or otherwise placed external to the pacemaker 20.

The lead 42, in addition to delivering stimulation pulses to the heart, presents electrical signals occurring within the heart 44, such as P-waves and R-waves (evidencing intrinsic cardiac activity of the atria and ventricles, respectively), to the timing and control circuits 34. Hence, for example, when programmed in a demand mode of operation, the pacemaker 22 is able to inhibit the generation of a pacing pulse 46 when intrinsic cardiac activity is sensed within a designated time period (the escape interval), in conventional manner.

A more complete description of the pacemaker chip 22 and its operation may be found in other documents. For example, U.S. Pat. Nos. 4,712,555 and 4,940,052 disclose the primary components of a conventional pacing system and teach the basic operation thereof.

In operation, the rate-responsive pacer 20 may operate in either a SENSOR ON mode or a SENSOR OFF mode. The selection of a desired mode of operation is controlled by the selector 30, shown functionally in FIG. 1 as a switch. The selector 30 connects a base rate signal on signal line 50 or a pacing rate signal on signal line 52 to the rate control signal line 48 of the pulse generator 32. Control of the selector 30 is obtained from the timing and control circuits 34, which control can be selected by an appropriate programming signal received from the programmer 38.

When the SENSOR OFF mode is selected, the selector 30 directs the base rate signal, generated by the timing and control circuits 34, to the rate control signal line 48 of the pulse generator 32. When the SENSOR ON mode is selected, the selector 30 directs the sensor-indicated rate (SIR) signal 52, generated by the processor 26, to the rate control signal line 48 of the pulse generator 32. The rate control signal, in turn, controls the pacing rate of the pacer 20 in conventional manner, e.g., by using the rate control signal to define a base escape interval.

In practice, the rate control signal 48 may be considered as the escape interval of the pacemaker, or at least as a signal that is responsible for generating a trigger pulse at the timing-out of the escape interval. As in conventional demand mode pacing, should intrinsic (natural) cardiac activity be sensed during the escape interval, no trigger pulse is generated and the timing circuits responsible for generating the escape interval are reset, thereby starting a new escape interval. Hence, regardless of the source of the rate control signal 48 (either the base rate signal 50 or the sensor-indicated rate signal 52), such signal can be overridden (if the pacemaker 20 is so programmed) by the sensing of natural cardiac activity.

As indicated, when the SENSOR ON mode is selected, the rate control signal 48 of the pulse generator 32 is connected by way of selector 30 to the sensor-indicated rate signal line 52 obtained from the output of processor 26. The sensor-indicated rate (SIR) signal is derived from a raw signal obtained from the sensor 24. The sensor 24 senses some type of parameter indicative of physiological need, such as physical activity, blood oxygen level, respiration rate, etc. Typically, the processor 26 includes means for converting the raw signal, appearing on signal line 54, to a sensor level index signal. This conversion may be accomplished in various ways, but typically a desired transfer characteristic, converting the sensor level index signal to an appropriate sensor-indicated rate signal, is stored or programmed into the memory 28 and used by the processor 26 to effectuate the conversion.

The SIR rate signal may be thought of as an escape interval that has a variable length or duration, which escape interval is used within the pacemaker chip 22 to define the pacing rate when the SENSOR ON mode is selected. For example, if the sensor 24 senses a moderately high level of physiological need, then the SIR signal 52 may define a relatively short escape interval, e.g., 500 msec, thereby ensuring that pacing pulses are delivered at least every 500 msec, or at a rate of approximately 120 ppm (corresponding to a paced heart rate of 120 bpm). On the other hand, if the sensor 24 senses a low level of physiological need, then the SIR signal 52 defines a relatively long escape interval, e.g., 1000 msec, thereby ensuring that a pacing pulse is delivered at least every second (1000 msec), or at a rate of approximately 60 ppm (corresponding to a paced heart rate of 60 bpm). In this manner, the rate at which stimulation pulses are provided to the heart on demand in the SENSOR ON mode varies as a function of the physiological need sensed by the sensor 24.

Regardless of whether the stimulation pulses are provided at a rate determined by the base rate signal 50 (sometimes referred to as the "programmed rate") or the sensor-indicated rate signal 52, a base escape interval, referred to herein as "$EI_0$", is defined by the appropriate pacemaker circuitry. The value of $EI_0$ is fixed in the SENSOR OFF mode (determined by the programmed rate), and the value of $EI_0$ is variable (determined by the sensor-indicated rate) in the SENSOR ON mode. The value of $EI_0$, in turn, determines the rate at which stimulation pulses are provided on demand to the heart.

Advantageously, a hysteresis mode of the present invention allows the heart more time to beat naturally before the pacemaker steps in with a stimulation pulse. From a circuitry standpoint, the hysteresis function is realized using any suitable device or method that extends the escape interval $EI_0$ to a new value, $EI_H$, where $EI_H$ is longer than the base value of $EI_0$, after the sensing of intrinsic activity, and returns the escape interval to its base value, $EI_0$, upon generating a pacing pulse. For the embodiment of a rate-responsive pacer as shown in FIG. 1, for example, the hysteresis function is typically realized in the timing and control logic 34 and/or the processor 26.

As mentioned previously, there are two types of pacemaker timing used with dual-chamber pacing modes, e.g., DDD pacing modes, whether such pacemakers are configured for providing rate-responsive functions or not. It is important to recognize that the present invention—which essentially provides for the adjustment of the pacemaker's base escape interval $EI_0$—has applicability to a wide variety of pacemakers and pacing modes, including dual-chamber pacemakers configured to use either of the two types of timing mentioned.

It will be recalled that a first type of dual-chamber pacemaker timing is an atrial-based timing system, wherein ventricular pacing, if provided at all, follows an atrial event by a prescribed amount (the AV Delay interval amount). The basic pacemaker timing, including the base escape interval of the pacemaker, is thus keyed off of atrial events, i.e., the sensing of a P-wave or the providing of an A-pulse.

It will also be recalled that a second type of dual-chamber pacemaker timing is a ventricular-based timing system, wherein ventricular pacing, if provided at all, follows the timing out of an AV Delay interval after an atrial event (P-wave or an A-pulse); and atrial pacing, if provided at all, follows the timing out of an Atrial Escape Interval following a ventricular event (R-wave or a V-pulse). The basic pacemaker timing is thus keyed off the sequence of atrial and ventricular events, with the Atrial Escape Interval usually being the parameter that is changed to vary the pacing rate, as it is by far the dominate parameter (in terms of length or duration) when compared to the AV Delay interval.

For simplicity of explanation, the description of the timing adjustments provided by the present invention are described below in terms of either a ventricular single-chamber device or dual-chamber atrial-based timing system. However, it is to be understood that such timing adjustments also have applicability to a dual-chamber ventricular-based timing system.

Figure 2:
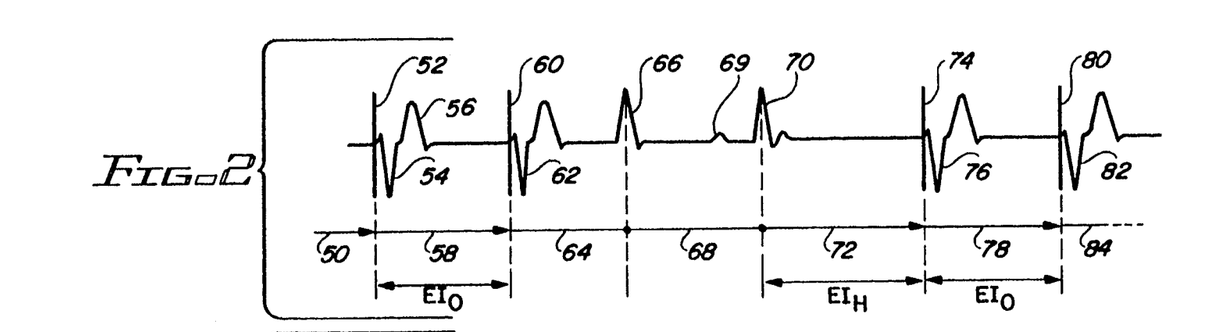
FIG. 2 is a simplified timing diagram that illustrates the manner in which the base escape interval of a rate-responsive single-chamber pacemaker is altered through the use of hysteresis.

Referring next to FIG. 2, a simplified timing waveform diagram is shown that illustrates the hysteresis mode of the present invention as used in a ventricular single-chamber system. It is noted that in FIG. 2, as well as in the other waveform timing diagrams presented herein, the basic cardiac waveforms associated with a patient's heart are shown in an upper trace; and the escape interval is shown in a lower trace. The horizontal axis of these waveform timing diagrams is in units of time, e.g., hundreds of milliseconds. The upper trace shows representative R-waves and P-waves, indicative of intrinsic cardiac activity, as well as paced P-waves or R-waves, responsive to a stimulation pulse. The lower trace shows the escape interval, with an arrow-head on the right of the escape interval indicating that the escape interval has timed-out; and a "dot" on the escape interval indicating that intrinsic cardiac activity was sensed prior to the timing-out of the escape interval.

Thus, for example, with reference to FIG. 2, it is seen that at the timing-out of a first escape interval 50, a stimulation pulse 52 is generated, causing a paced R-wave 54 to occur. The paced R-wave 54 evidences the depolarization and contraction of the appropriate ventricular tissue. A short time after the paced R-wave 54, a T-wave 56 occurs, evidencing the repolarization of the ventricular tissue. (For purposes of the present invention, the presence of the T-wave is not important, except to the extent that it shows the ventricular tissue must repolarize before it can again be depolarized and contract. It is also noted that the waveform diagrams depict the T-wave as being much more pronounced following a paced R-wave, i.e., following a forced contraction, than following an intrinsic or natural contraction.)

The generation of the stimulation pulse 52 causes the pacemaker's escape interval to start again. Hence, a second escape interval 58 begins upon the generation of the stimulation pulse 52. The second escape interval 58 has a duration or length of $EI_0$. The value of $EI_0$ may be a minimum programmed rate or a rate derived from a sensor-indicated rate. For the condition shown in FIG. 2, the escape interval 58 also times-out, causing another stimulation pulse 60 to be generated, followed by another paced R-wave 62. Thus, the stimulation pulses 52 and 60 are generated at a rate determined by $EI_0$.

After the generation of the stimulation pulse 60, a third escape interval 64 begins. However, before the timing-out of the escape interval 64, a natural R-wave 66 is detected, evidencing intrinsic cardiac activity. The natural R-wave 66 causes a new escape interval 68 to start its timing cycle. The occurrence of the natural R-wave 66 also triggers the hysteresis mode of the present invention. In such mode, the escape interval 68 is extended and has a duration, $EI_H$, where $EI_H$ is greater (longer) than $EI_0$.

For the condition shown in FIG. 2, before the extended escape interval 68 times-out, another natural R-wave 70 is detected. (Also seen in FIG. 2 is a P-wave 69 that precedes the R-wave 70.) The occurrence of the R-wave 70 starts a new extended escape interval 72. The escape interval 72 also has a value $EI_H$. For the example shown in FIG. 2, the escape interval 72 times-out before any intrinsic cardiac activity is sensed. Hence, upon the timing-out of the escape interval 72, a stimulation pulse 74 is generated, evoking a paced R-wave 76. The generation of the stimulation pulse 74 causes another escape interval 78 to begin. In accordance with the hysteresis mode of the invention, however, the value of the escape interval 78 is returned to $EI_0$. For the example shown in FIG. 2, the escape interval 78 times-out before any natural cardiac activity is sensed. Hence, a stimulation pulse 80 is generated, evoking another paced R-wave 82, and causing another escape interval 84 to begin.

Thus, as described above, the hysteresis mode of the present invention extends the basic escape interval $EI_0$, whether derived from a programmed minimum rate or determined from a sensor-indicated rate, to a new value $EI_H$ in response to sensed intrinsic (natural) cardiac activity; and returns the value of the escape interval to $EI_0$ from $EI_H$ in response to generating a stimulation pulse. The stimulation pulse, in turn, is generated upon the timing-out of the escape interval $EI_H$ without sensing intrinsic cardiac activity.

Figure 3:
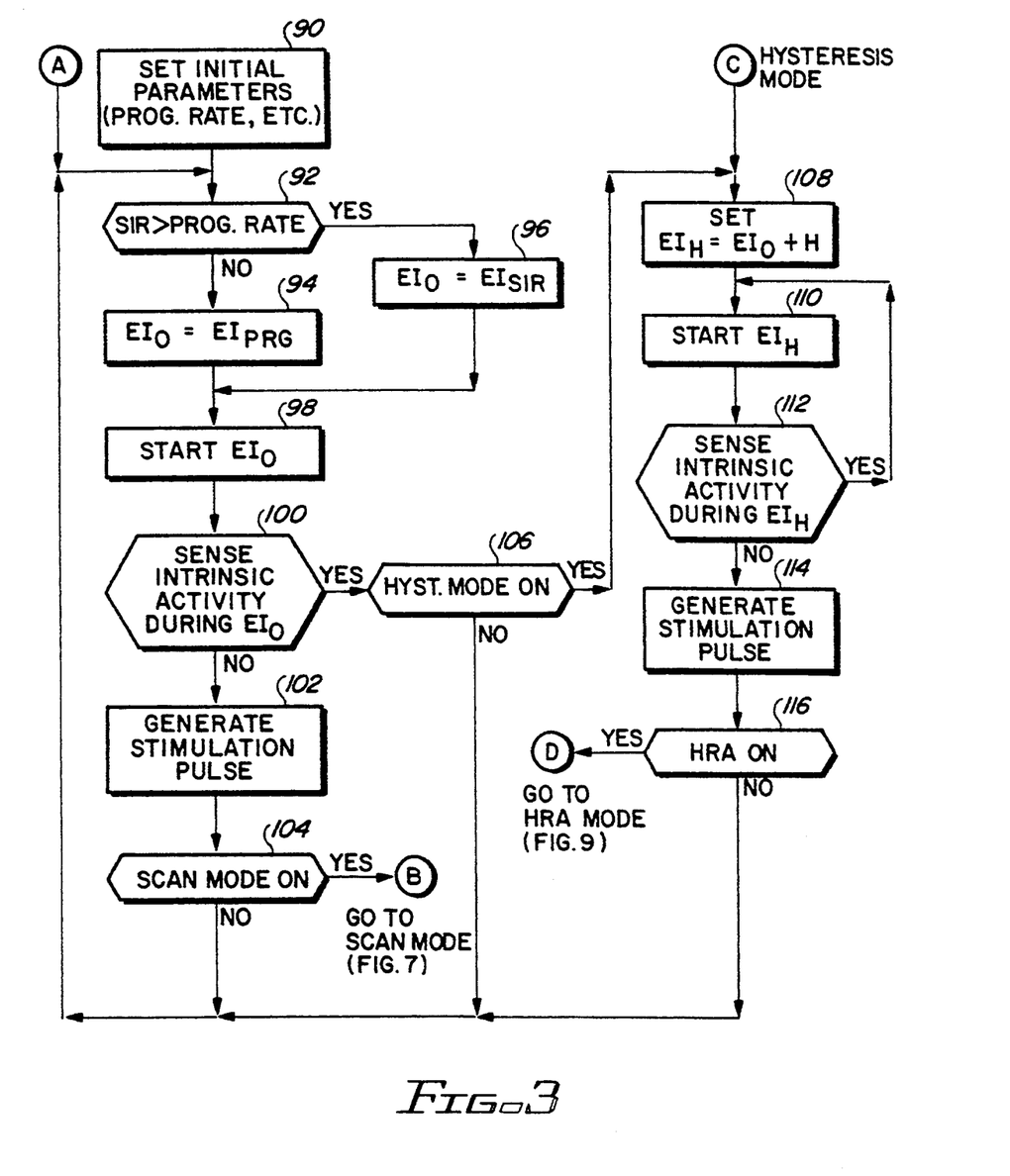
FIG. 3 is a flowchart of the operation of a pacemaker that utilizes a hysteresis mode in accordance with the present invention.

Referring next to FIG. 3, there is shown a flowchart that illustrates the operation of the pacemaker of FIG. 1 in accordance with the present invention. In FIG. 3, and the other flowcharts presented herein (FIGS. 7 and 9), each major step or decision of the illustrated operation is depicted as a "block." Each block has a reference number attached thereto, which reference number is used in the description(s) that follow. Those of skill in the art, given the descriptions and information presented herein, can readily implement a pacemaker having a hysteresis and other modes as described herein.

As seen in FIG. 3, a first step of the invention relates to setting the initial parameters (block 90). Any programmable pacemaker has a wide variety of operating parameters associated therewith, as is known and described in the literature. For purposes of the present invention, such programmable parameters include the pacemaker's programmed minimum rate and whether the hysteresis mode, and other modes, such as the scan mode and hysteresis rate adjust (HRA) mode, are to be programmed ON or OFF. If programmed ON, certain parameters associated with these modes are also set, such as the hysteresis rate, the scan increment, the scan frequency, the HRA step size, etc. In this regard, it should be noted that it is common practice in the pacemaker art to refer to the pacemaker's programmed minimum rate, and the hysteresis rate, in terms of a frequency expressed in pulses per minute (ppm), which frequency is directly relatable to a heart rate, usually expressed in terms of beats per minute (bpm). However, in the operation of the pacemaker and, in particular, when referring to the escape interval, it is most common to refer to a time interval, in units of seconds or milliseconds (msec). The escape interval is thus simply the period associated with the applicable programmed or sensor-indicated rate. Thus, for example, a rate of 60 ppm translates to an escape interval of 1000 msec; and a rate of 100 ppm translates to an escape interval of 600 msec. Thus, the slower the programmed or sensed frequency, the longer the escape interval. Similarly, the faster the programmed or sensed frequency, the shorter the escape interval, one being inversely proportional to the other.

Thus, in setting the initial parameters (block 90 of FIG. 3), the programmed minimum rate is typically expressed and programmed in terms of ppm, such as 60 ppm. The hysteresis rate may likewise be programmed in terms of ppm, at a rate lower than the programmed minimum rate, such as 50 ppm. Alternatively, in a rate-responsive pacemaker, the hysteresis rate may be expressed in terms of a variance of or change in the programmed minimum rate or the sensor-indicated rate, whichever rate is applicable, expressed in ppm, milliseconds (ms) or a percentage of the programmed rate. For example, the hysteresis rate may be expressed as a 10 ppm or a 10% decrease in the applicable rate or a 100 ms increased in the paced cycle length. Step sizes may also be expressed in terms of ppm, ms or a percentage of a base rate. However, as will be evident from the descriptions that follow, even though these programmable parameters are normally expressed and programmed in terms of a rate, or a rate change, it is noted that all such parameters are eventually converted by the pacemaker logic and processing circuits to a corresponding time interval, or change in time interval, of the applicable period.

Once the initial parameters have been set (block 90), then the pacemaker determines whether the sensor-indicated rate (SIR), as determined by the sensor 24 (FIG. 1), is greater than the programmed minimum rate (block 92). If no, then the base escape interval, $EI_0$, is set equal to a programmed escape interval, $EI_{PRG}$, determined from the programmed minimum rate (block 94). If yes, then the base escape interval, $EI_0$, is set equal to a sensor-indicated rate escape interval, $EI_{SIR}$, determined from the sensor-indicated rate (block 96). In this way, the value of the base escape interval, $EI_0$, is determined by the greater of the SIR signal or the programmed minimum rate.

Once the value of the base escape interval has been determined, then the base escape interval $EI_0$ is started (block 98), i.e., a timer starts to time-out a time period, or time window, equal to the value of the base escape interval. If the $EI_0$ time window times-out without sensing any intrinsic cardiac activity, as determined at block 100, then a stimulation pulse is generated (block 102). Upon generating the stimulation pulse, a determination is made as to whether the scan mode is ON (block 104). If not, then the process begins again (block 92), i.e., an escape interval value $EI_0$ is determined (blocks 92, 94 and 96), and the escape interval period is started (block 98).

Should intrinsic cardiac activity be sensed during the timing-out of the base escape interval $EI_0$ (block 100), then a determination is made as to whether the hysteresis mode is programmed ON (block 106). If no, then the generation of a stimulation pulse inhibited, and the process begins again (blocks 92, 94, 96, 98). If yes, then the escape interval $EI_0$ is extended to a hysteresis value $EI_H$ (block 108). That is, the hysteresis value of the escape interval $EI_H$ is determined by the relationship $$EI_H = EI_0 + H,$$

where H is a hysteresis factor determined, e.g., as a prescribed percentage of the base escape interval $EI_0$, or some other suitable relationship. Suppose, for example, that H is selected to be 10% of the escape interval $EI_0$, and that the escape interval $EI_0$ is 1000 msec. $EI_H$ would thus be $$EI_H = 1000 + 0.10(1000) = 1100 \text{ msec},$$

corresponding to a hysteresis rate of roughly 55 ppm. Should $EI_0$ be much shorter, e.g., 600 msec, corresponding to a sensor-indicated rate of 100 ppm, and assuming that H is still selected to be 10% of the escape interval $EI_0$, then $EI_H$ would be $$EI_H = 600 + 0.10(600) = 660 \text{ msec},$$

corresponding to a hysteresis rate of roughly 91 ppm.

Once the value of the hysteresis escape interval $EI_H$ is determined, the hysteresis escape interval $EI_H$ is started (block 110), i.e., a timer starts to time-out a time period, or time window, equal to the value of the hysteresis escape interval $EI_H$. If intrinsic cardiac activity is sensed before the escape interval $EI_H$ times-out (block 112), then $EI_H$ is reset and restarted to time-out again (blocks 110, 112). In this manner, so long as intrinsic cardiac activity continues to be sensed (block 112), the escape interval remains set to $EI_H$, and the heart is afforded a longer time period or time window within which it may beat on its own before a stimulation pulse is generated. If intrinsic cardiac activity is not sensed before the timing-out of the escape interval $EI_H$ (block 112), then a stimulation pulse is generated (block 114). If the HRA mode is not ON (block 116), then the process starts over again by determining an appropriate value of $EI_0$ (blocks 92, 94, 96) and restarting such value as the next escape interval (block 98). In this manner, upon the failure to sense intrinsic activity (block 112), and assuming the HRA mode is not ON, the escape interval returns to the base value $EI_0$.

Figure 4:
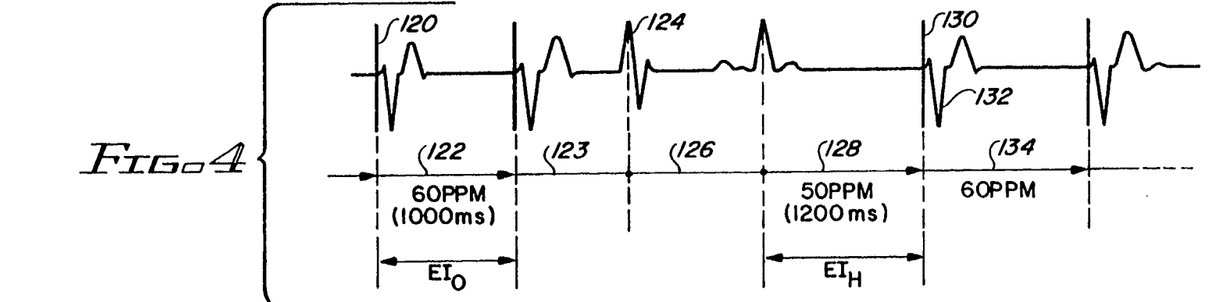
FIG. 4 is a timing waveform diagram that illustrates an example of the cardiac activity and escape interval associated with the hysteresis mode of the invention when the programmed pacing rate is greater than or equal to the sensor-indicated rate.
Figure 5:
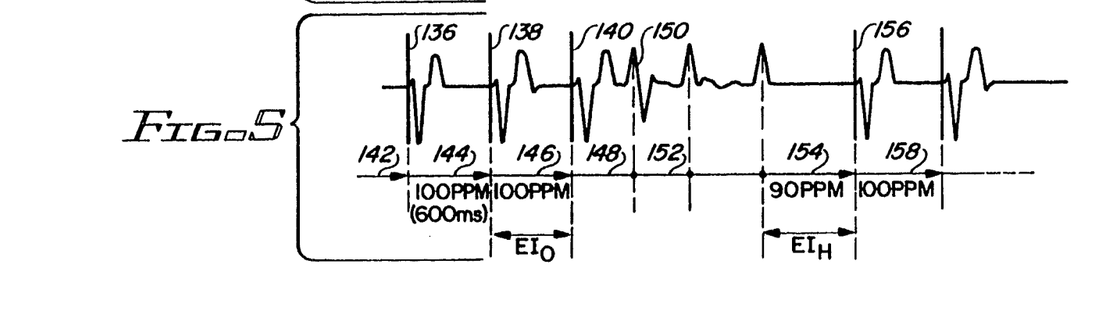
FIG. 5 is a timing waveform diagram that illustrates an example of the cardiac activity and escape interval associated with the hysteresis mode of the invention when the programmed pacing rate is less than the sensor-indicated rate.

To further illustrate the operation of the hysteresis mode, reference is made to FIGS. 4 and 5. FIG. 4 is a timing waveform diagram that illustrates operation of the hysteresis mode when the sensor-indicated rate is less than or equal to the programmed base rate, i.e., when the determination made at block 92 of FIG. 3 is NO. Similarly, FIG. 5 is a timing waveform diagram that illustrates the hysteresis mode when the sensor-indicated rate is greater than the programmed base rate, i.e., when the determination made at block 92 of FIG. 3 is YES.

As seen in FIG. 4, a stimulation pulse 120 is provided at the programmed base rate, which (for the example shown in FIG. 4) is assumed to be 60 ppm. Thus, the value of $EI_0$ is set to 1000 msec, and an escape interval 122 having this duration is generated. When an intrinsic R-wave 124 occurs prior to the timing-out of the next escape interval 123, the duration of the new escape interval 126 is extended to $EI_H$, which (for the example shown in FIG. 4) is assumed to be 1200 msec, corresponding to a hysteresis rate of 50 ppm. From that point forward, for so long as intrinsic R-waves continue to be sensed, all subsequent escape intervals, such as the escape intervals 126 and 128, have a duration of $EI_H$. If the escape interval $EI_H$ times-out without detecting an R-wave, such as is shown relative to the escape interval 128, then a stimulation pulse 130 is generated, invoking a paced R-wave 132. The generation of the stimulation pulse 130 causes the value of the next escape interval 134 to decrease to $EI_0$, which (for the example shown in FIG. 4) is the programmed base rate of 60 ppm.

FIG. 5 follows a similar pattern as is shown in FIG. 4 except that the escape interval $EI_0$ is set by the sensor-indicated rate. For the example shown in FIG. 5, the sensor-indicated rate is assumed to be 100 ppm, causing the escape interval $EI_0$ to assume a value of 600 msec. For the first portion of the waveform shown in FIG. 5, stimulation pulses 136, 138 and 140 are generated at the timing-out of the escape intervals 142, 144, and 146, respectively. Prior to the termination of escape interval 148, however, a natural R-wave 150 is detected. This causes the value of the next escape interval 152 to be extended to the hysteresis value, which (for purposes of the example shown in FIG. 5) is assumed to be 10 ppm less than the value of the sensor-indicated rate. Thus, assuming a sensor-indicated rate of 100 ppm, the hysteresis value of the escape interval $EI_H$ is extended to a value that corresponds to a rate of 90 ppm, or about 667 msec. The escape interval remains at this hysteresis value of $EI_H$ for so long as intrinsic cardiac activity is sensed before the escape interval $EI_H$ times-out. As illustrated in FIG. 5, intrinsic cardiac activity continues for a few cycles until escape interval 154 times-out without detecting an intrinsic R-wave. The timing-out of escape interval 154 causes a stimulation pulse 156 to be generated, and thereafter the next escape interval 158 is reduced to its sensor-indicated rate value (of 100 ppm for the example shown). The escape interval remains at this value until intrinsic cardiac activity is again sensed.

Figure 6:
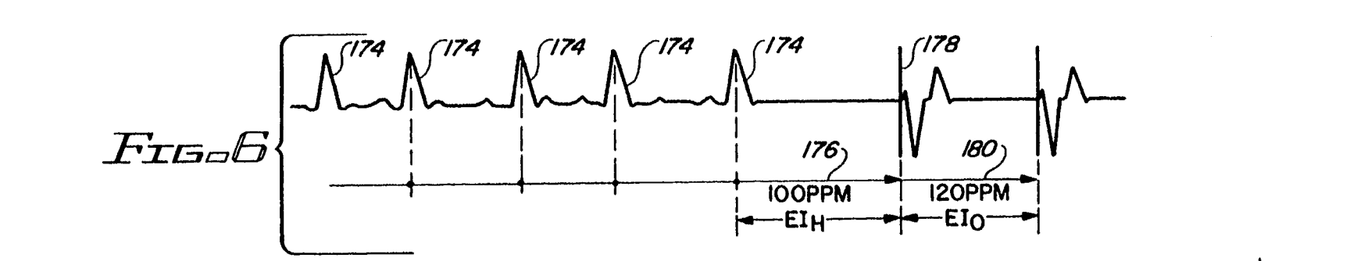
FIG. 6 is a timing waveform diagram that illustrates an example of the termination of the hysteresis mode.

FIG. 6 shows a timing waveform diagram that illustrates the termination of rate-responsive hysteresis in accordance with the present invention. In FIG. 6, it is assumed that the hysteresis rate is 100 ppm, corresponding to a hysteresis escape interval $EI_H$ of 600 msec. As long as intrinsic R-waves 174 continue to be sensed before the timing-out of the escape interval $EI_H$, then no stimulation pulse is generated, and the hysteresis mode continues. The hysteresis mode terminates, as indicated previously, when an escape interval 176, having a duration of $EI_H$, times-out without sensing intrinsic activity. When this occurs, a stimulation pulse 178 is generated, and the next escape interval 180 returns to its base value, $EI_0$, which (for the example shown in FIG. 6) is 500 msec (corresponding to a sensor-indicated rate of 120 ppm).

Returning to FIG. 3 momentarily, two additional operating modes of the invention are depicted: a scan mode (block 104) and a hysteresis rate adjust mode (block 116). The scan mode, when programmed ON, is used to gradually increase the escape interval $EI_0$, before entering the hysteresis mode (i.e., before intrinsic cardiac activity is sensed), in order to afford a slightly longer time window (escape interval) in which intrinsic cardiac activity may occur prior to the generation of the next stimulation pulse, thereby effectively scanning for intrinsic rhythm. The hysteresis rate adjust (HRA) mode, when programmed ON, is used to gradually return the escape interval from $EI_H$ to $EI_0$ after the hysteresis mode has been entered (by sensing intrinsic cardiac activity) and terminated (by the timing-out of $EI_H$ without having sensed intrinsic activity). These two modes are explained in more detail below in connection with FIGS. 7 and 9.

In the scan mode, the pacemaker automatically increases the pacing interval, thereby scanning for intrinsic rhythm. If any cardiac activity is detected during the scan cycle, the hysteresis mode is initiated. The pacing interval is increased by increasing (lengthening) the programmed escape interval. The increase in the pacing interval is a programmable parameter and the selection may be programmed either in ppm, milliseconds or a percent of the cycle length. Further, it should be noted that the scan mode is tied directly to the sensor function, if enabled. That is, the base pacing interval $EI_0$ that is lengthened by operation of the scan mode will be, as shown in FIG. 3 (blocks 92, 94, 96), the greater of the sensor-indicated rate or the programmed rate. Alternatively, the feature can be set to activate only when the device is functioning at the basic programmed rate.

Figure 7:
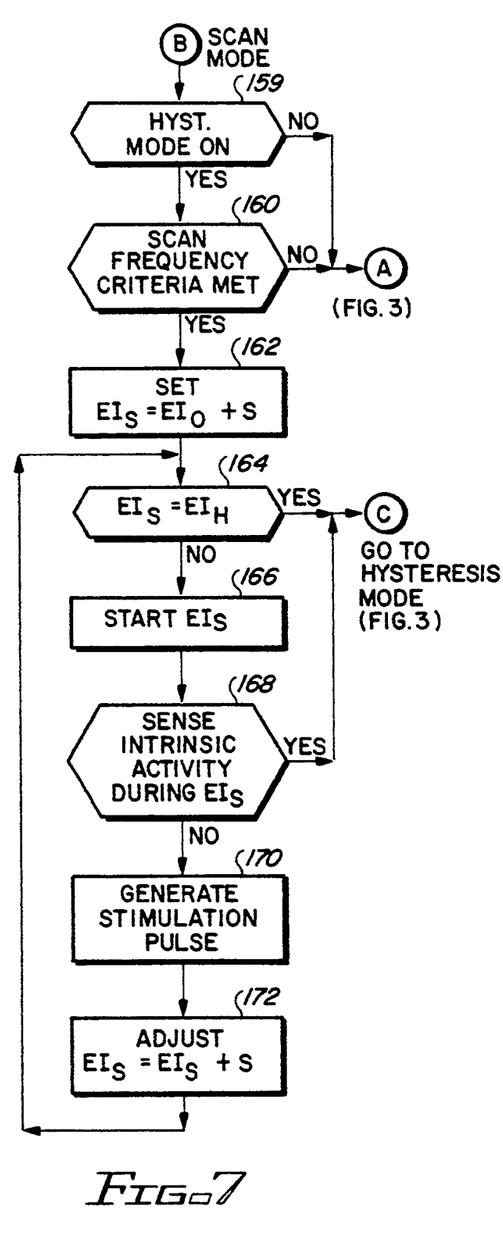
FIG. 7 is a flowchart that depicts the scan mode of operation of the invention, referenced in FIG. 3.

Referring then to FIG. 7, a simplified flowchart of the scan mode is shown. Once the scan mode is initiated, a preliminary step involves a determination as to whether the hysteresis mode is on (block 159). There is no reason to invoke the scan mode unless the hysteresis mode is enabled. A next step involves a determination as to whether the scan frequency criteria has been met (block 160). The scan frequency criteria relates to the scan frequency, or how often the pacemaker enacts an automatic rate change (increasing of the pacing interval in order to scan for intrinsic rhythm) when the scan mode is programmed ON. The scan frequency is a programmable parameter that may be programmed in seconds, minutes, hours, days or a specified number of paced events. For example, if the scan frequency is programmed to 30 minutes, then every 30 minutes the pacemaker would go through the scan mode shown in FIG. 7.

If the scan frequency criteria is met (block 160), then the escape interval is increased to a new value $EI_S$ (block 162). The value of $EI_S$ is preferably determined to be an incremental increase from the base escape interval $EI_0$ (which value of $EI_0$, as described above, may be determined from either the programmed rate or the sensor-indicated rate). That is, $$EI_S = EI_0 + S$$

where S is an incremental step size for the scanning function. As indicated above, the value of S is a programmable parameter, or is derived from a programmable parameter.

Once the scan escape interval $EI_S$ has been defined (block 162), a determination is made as to whether $EI_S$ has been increased to a maximum value (block 164). Of course, if the scan mode has just been initiated, the maximum value of $EI_S$ will not have been reached yet. However, if the scan mode has been operational for several cycles, the value of $EI_S$ may have increased to a maximum allowed value, in which case the scan mode is terminated by initiating the hysteresis mode (beginning at block 108 in FIG. 3). It is noted that if intrinsic activity has not been detected after the pacing interval has been increased to its maximum value, and if intrinsic activity is not sensed during the first cycle of the hysteresis mode, then the hysteresis mode immediately terminates, and the escape interval returns to its base value, $EI_0$, as indicated in FIG. 6.

For the example shown in FIG. 7, it is assumed that the maximum value to which the scan escape interval $EI_S$ may be increased is $EI_H$, the hysteresis escape interval value. However, it is to be understood that this is only exemplary, and any value may be programmed as the maximum value of $EI_S$.

Once a value of $EI_S$ has been defined, the escape interval defined by this value is started (block 166). If intrinsic cardiac activity is sensed during $EI_S$, i.e., before the timing-out of $EI_S$, then the hysteresis mode is initiated (block 168). However, if no intrinsic cardiac activity is sensed during $EI_S$, then a stimulation pulse is generated as soon as $EI_S$ times-out (block 170). The value of $EI_S$ is then increased by the programmed incremental step size, S (block 172), and the process repeats (blocks 164, 166, 168, 170). In this manner, the scan escape interval $EI_S$ is incrementally increased until either intrinsic cardiac activity is sensed, or until $EI_S$ reaches its maximum value.

Figure 8:
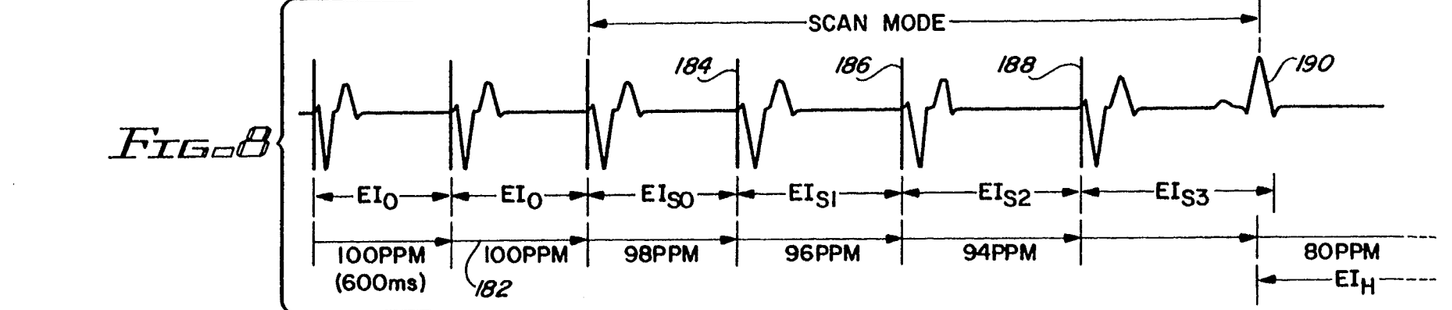
FIG. 8 is a timing waveform diagram that illustrates one example of the scan mode shown in FIG. 7.

A timing waveform diagram illustrating an example of the operation of the scan mode is shown in FIG. 8. In the example of FIG. 8, it is assumed that the base escape interval, $EI_0$, is 600 msec, corresponding to a sensor rate of 100 ppm. It is also assumed that the hysteresis offset is set to 20 ppm, meaning that the hysteresis rate is to be 20 ppm less than the sensor rate. Further, it is assumed that the incremental scan step size, S, is programmed to correspond to 2 ppm. Thus, as seen in FIG. 8, the scan mode begins by increasing the escape interval to a value $EI_{S0}$, where the value of $EI_{S0}$ corresponds to a rate of 98 ppm. Because no intrinsic activity is sensed during $EI_{S0}$, a stimulation pulse 184 is generated. The next escape interval, $EI_{S1}$, is increased an incremental amount so as to correspond to a rate of 96 ppm. Again, no intrinsic activity occurs, so another stimulation pulse 186 is generated. The following escape interval, $EI_{S2}$, is increased by the scan step amount, corresponding to a rate of 94 ppm. Because no intrinsic activity is sensed, yet another stimulation pulse 188 is generated. The following escape interval, $EI_{S3}$, is again increased by the scan step amount so as to correspond to a rate of 92 ppm. However, before $EI_{S3}$ times-out, an R-wave 190 is sensed. Thus, the scan mode terminates, and the hysteresis mode begins with an escape interval $EI_H$ corresponding to a rate of 80 ppm.

Figure 9:
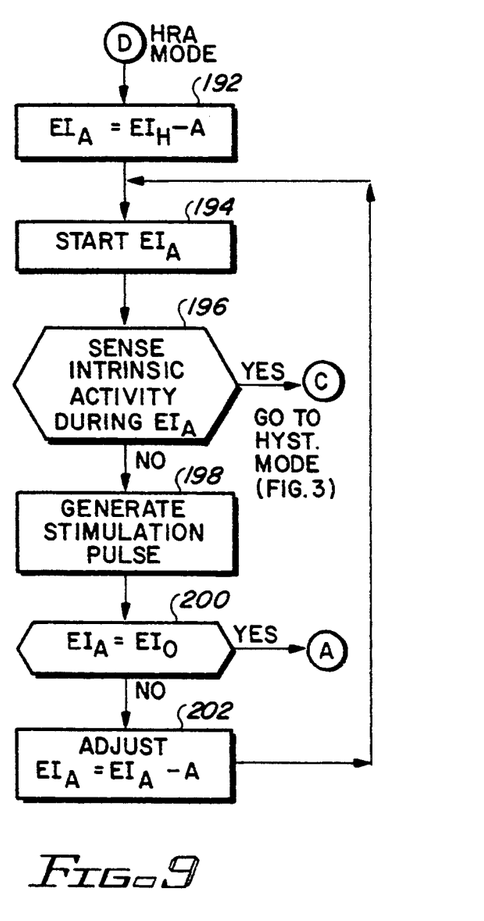
FIG. 9 flowchart that depicts the hysteresis rate adjust (HRA) mode of the invention, referenced in FIG. 3.

Referring next to FIG. 9, a flowchart of the hysteresis rate adjust (HRA) mode of the invention is illustrated. The HRA mode is intended to allow for a smooth transition from the hysteresis mode response to the sensor driven response. This is done by providing a gradual decrease from the hysteresis escape interval $EI_H$ to the base escape interval $EI_0$. This change corresponds to a gradual increase from the hysteresis rate to the sensor-indicated rate or programmed rate, whichever is greater. The HRA mode may be programmed ON or OFF, as indicated at block 116 of FIG. 3. The number of stimulation pulses over which the change from $EI_H$ to $EI_0$ is controlled by a programmable parameter that may be programmed in terms of the number of pulses, a time interval (seconds), or a fixed rate increment.

As described above in connection with FIG. 3, the HRA mode is initiated via the output stimulus at the end of the hysteresis interval (blocks 114, 116 of FIG. 3). Once initiated, an HRA escape interval, $EI_A$, is defined (block 192 of FIG. 9). The value of $EI_A$ is typically defined to be a function of the value of $EI_H$. For example, as shown in FIG. 9, $EI_A$ is defined as $$EI_A = EI_H - A$$

where A is derived from the programmed parameter that specifies how quickly the transition from $EI_H$ to $EI_0$ is to be made.

Once the value of $EI_A$ is defined, an escape interval having this value is started (block 194). If cardiac activity is sensed during $EI_A$ (block 196), i.e., before $EI_A$ times-out, then the hysteresis mode is invoked (FIG. 3). If cardiac activity is not sensed during $EI_A$, then a stimulation pulse is generated (block 198). A determination is then made as to whether $EI_A$ has reached its destination value, $EI_0$ (block 200). If not, then the value of $EI_A$ is adjusted to bring it incrementally closer to its destination value (block 202), and the process repeats (blocks 194, 196, 198 and 200). If the value of $EI_A$ has reached its destination value, i.e., if $EI_A = EI_0$, then the HRA mode terminates.

Figure 10:
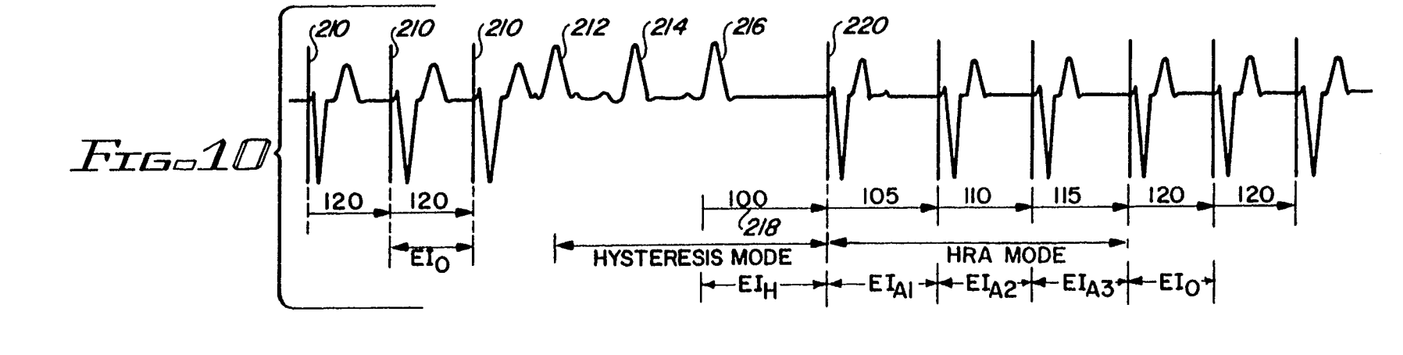
FIG. 10 is a timing waveform diagram that depicts one example of the HRA mode of operation of FIG. 5.

FIG. 10 shows a timing waveform diagram that depicts an example of the HRA mode of operation shown in FIG. 9. For the example shown in FIG. 10, it is assumed that the sensor-indicated rate is 120 ppm, the hysteresis offset is 20 ppm (i.e., the hysteresis rate is 20 ppm less than the sensor-indicated rate), and the hysteresis rate adjust transition is to occur in 4 pulses (5 ppm increments).

As seen in FIG. 10, the pacemaker is initially operating in the conventional rate-responsive mode, providing stimulation pulses 210 at the conclusion of the escape interval $EI_0$. Upon the occurrence of intrinsic R-wave 212, the hysteresis mode begins, causing the escape interval to increase (lengthen) to $EI_H$. Two additional intrinsic R-waves 214 and 216 are sensed during the hysteresis mode. However, the hysteresis mode terminates, and the HRA mode beings, when the escape interval 218 times-out without the occurrence of intrinsic activity, thus causing the stimulation pulse 220 to be generated. In accordance with the programmed HRA mode, the pulse 220 is counted as the first pulse of the transition period. The stimulus 220 is followed by escape intervals $EI_{A1}$, $EI_{A2}$, and $EI_3$, each followed by a corresponding stimulation pulse, derived to provide a smooth transition from $EI_H$ to $EI_0$. For example, $EI_{A1}$ has a value corresponding to a pacing rate of 105 ppm, $EI_{A2}$ corresponding to a value of 110 ppm, and $EI_{A3}$ corresponding to a value of 115 ppm. Following the stimulus after $EI_{A3}$, the HRA mode terminates because the next value of the escape interval is equal to $EI_0$.

In the prior art, hysteresis has been typically used only with single-chamber pacing. Thus, the hysteresis mode is initiated by an event detected in the pacing chamber. That is, for VVIR pacing it is ventricular activity that triggers the hysteresis mode, while for AAIR pacing it is atrial activity that triggers the hysteresis mode. In accordance with the present invention, when dual-chamber pacing is utilized, the hysteresis mode should be initiated only when a sensed event is detected in the atrial chamber. In this manner, the pacemaker has the ability to shift into the hysteresis mode of operation while still maintaining the ability to synchronize to the atrial rate.

Figure 11:
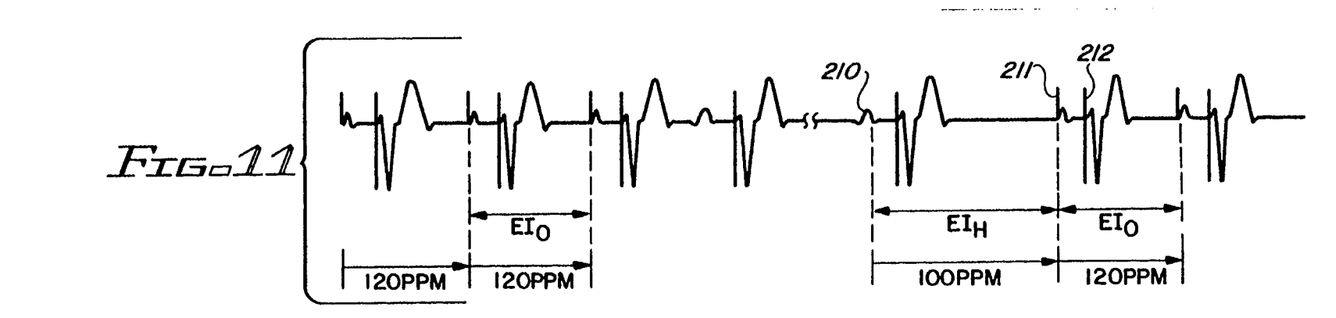
FIG. 11 shows a timing waveform diagram that illustrates DDD rate-responsive pacing with hysteresis in accordance with the present invention.

An example of DDD rate-responsive pacing having a hysteresis mode in accordance with the present invention is shown in FIG. 11. The example shown in FIG. 11 assumes that the sensor rate is 120 ppm and that the hysteresis offset is 20 ppm. As seen at the left side of the waveform, the sensor driven rate of 120 ppm controls the heart rate. However, an atrial event, i.e., a P-wave 210, is detected before the timing-out of the escape interval $EI_0$, which escape interval defines the sensor-driven rate of 120 ppm. The occurrence of such atrial event triggers the hysteresis mode, extending the escape interval to its hysteresis value, $EI_H$, allowing the heart to beat at a rate of 100 bpm. If the intrinsic cardiac (atrial) rate falls below 100 bpm, i.e., if atrial activity is not sensed before the timing-out of the hysteresis escape interval, $EI_H$, then stimulation pulse 211 is generated and the hysteresis mode terminates, and the escape interval returns to $EI_0$.

Figure 12:
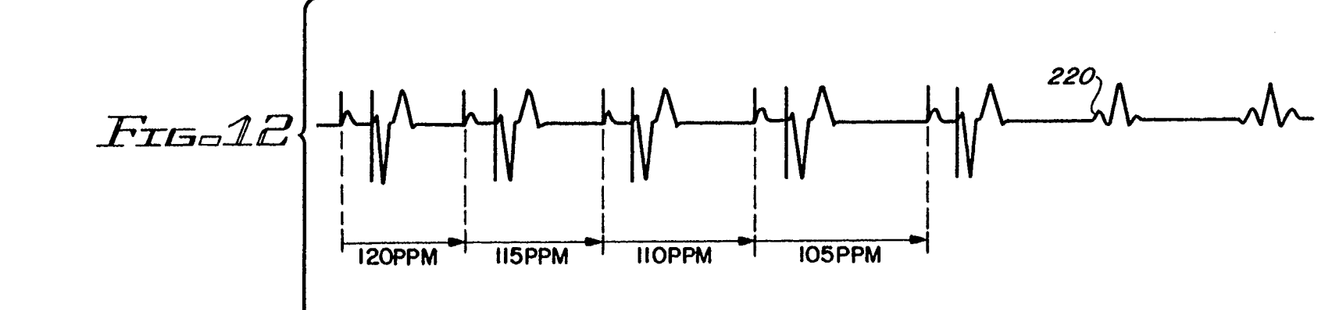
FIG. 12 is a timing waveform diagram that illustrates the scan mode as applied to DDD rate-responsive pacing in accordance with the present invention.

An example of DDD rate-responsive pacing having both the hysteresis mode and the scan mode of operation enabled in accordance with the present invention is depicted in FIG. 12. The example shown in FIG. 12 assumes a sensor-indicated rate of 120 ppm, a hysteresis offset of 20 ppm, and a scan interval of 5 ppm. Initially, the sensor-indicated rate of 120 ppm controls the pacing rate. However, as soon as the scan mode begins, the escape interval is incrementally lengthened, in intervals corresponding to 5 ppm steps, until intrinsic atrial activity is detected, as manifest by the P-wave 220, or the maximum set interval is reached. The sensing of the P-wave 220 triggers the hysteresis mode, and the hysteresis mode continues for so long as intrinsic atrial activity remains at a rate greater than or equal to 100 bpm (hysteresis rate). During this time, P-wave synchronous pacing is advantageously allowed to occur without interference from the pacemaker.

Figure 13:
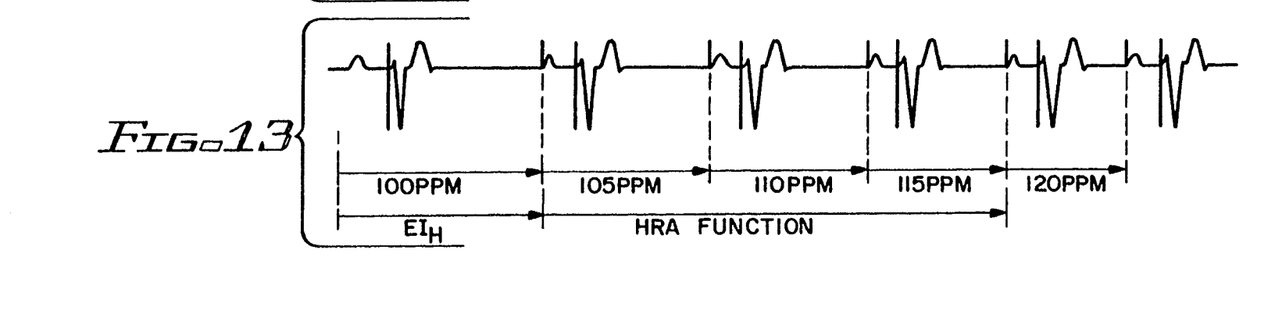
FIG. 13 is a timing waveform diagram that depicts the HRA mode as applied to DDD rate-responsive pacing in accordance with the present invention.

An example of DDD rate-responsive pacing having the hysteresis mode and the HRA mode enabled is shown in FIG. 13. For the example shown in FIG. 13, it is assumed that the sensor-indicated rate is 120 ppm, the hysteresis offset is 20 ppm, and the number of HRA pulses is 4 (decrement of 5 ppm). The hysteresis mode terminates upon the failure of atrial activity to be sensed within the escape interval $EI_H$. In accordance with the HRA scan mode, the next escape interval is set to a value corresponding to 105 ppm, and so on, until the escape interval has been decreased (shortened) after 4 stimulation pulses so as to correspond to a rate of 120 ppm. Should another sensed atrial event have occurred, the hysteresis mode would again have been entered.

As described above, it is thus seen that the present invention provides a hysteresis mode that may be programmably selected for use in a single- or dual-chamber rate-responsive pacer and/or a non-rate-responsive single- or dual-chamber pacer. Such hysteresis mode advantageously affords the heart the opportunity to beat at its own rhythm more often, even in the presence of a varying escape interval set, e.g., by a physiologic sensor, thereby also enhancing the longevity of the pacemaker by reducing the number of stimulation pulses that the pacer must generate.

As also described above, it is seen that the present invention provides a scan mode of operation for use with a rate-responsive or other pacer. Such scan mode advantageously extends (lengthens) the basic escape interval of the pacer in small incremental steps when no intrinsic cardiac activity is sensed during the prior escape interval, thereby providing an increasingly longer window of time wherein intrinsic cardiac activity may occur before a stimulation pulse is generated.

As further described above, it is seen that the present invention provides a hysteresis rate adjust (HRA) mode of operation for use with a hysteresis mode of operation in a rate-responsive or other pacer. Such HRA mode advantageously returns the operation of the pacer from the hysteresis mode to a normal rate-responsive mode in a gradual fashion, over several pacing cycles, rather than making this change in a single step, as is common in the prior art.

While the invention herein disclosed has been described by means of specific embodiments and applications thereof, numerous modifications and variations could be made thereto by those skilled in the art without departing from the scope of the invention set forth in the claims.

What is claimed is:

1. A rate-responsive pacemaker comprising:
  sensing means for sensing cardiac activity; pulse generator means for generating pacing pulses at a rate set by a rate control parameter in the absence of sensed intrinsic cardiac activity;
  means for generating a programmed rate parameter;
  sensor means for generating a sensor signal, said sensor signal varying as a function of a sensed physiological parameter;
  means for providing a sensor-indicated rate (SIR) parameter as a function of said sensor signal;
  selection means for selecting the greater one of said programmed rate parameter or said SIR parameter as the rate control parameter for said pulse generator means; and hysteresis means for adjusting said rate control parameter upon sensing cardiac activity so that sensed intrinsic cardiac activity can occur.

2. The rate-responsive pacemaker, as set forth in claim 1, wherein said rate control parameter comprises an escape interval, said escape interval comprising at least one period of time derived from said programmed rate parameter or said SIR parameter as determined by said selection means, pacing pulse being generated at the conclusion of the escape interval unless intrinsic cardiac activity is sensed during said escape interval.

3. The rate-responsive pacemaker, as set forth in claim 2, wherein said hysteresis means comprises means for initiating a hysteresis mode of operation, said hysteresis mode of operation causing a first escape interval to be used following the generation of a pacing pulse, and a second escape interval to be used following the sensing of intrinsic cardiac activity, said first escape interval being no longer than said second escape interval.

4. The rate-responsive pacemaker, as set forth in claim 3, wherein said hysteresis mode of operation may be programmably turned ON or OFF.

5. The rate-responsive pacemaker, as set forth in claim 3, further including scan means for incrementally increasing said first escape interval after each pacing pulse until said first escape interval is equal to said second escape interval.

6. The rate-responsive pacemaker, as set forth in claim 5, wherein said scan means may be selectively programmed ON or OFF.

7. The rate-responsive pacemaker, as set forth in claim 3, further including hysteresis rate adjustment means for gradually decreasing the second escape interval after the occurrence of a pacing pulse, said decreasing of the second escape interval continuing until said second escape interval is approximately equal to said first escape interval.

8. The rate-responsive pacemaker, as set forth in claim 7, wherein said hysteresis rate adjustment means may be selectively programmed ON or OFF.

9. An implantable rate-responsive pacemaker comprising:

sensor means for sensing a physiological parameter and providing a sensor-indicated rate (SIR) signal indicative of said physiological parameter;

timing means for generating an escape interval having a normal duration that varies as a function of said SIR signal;

pulse generator means for generating a stimulation pulse upon the timing-out of said escape interval;

reset means for resetting said escape interval upon the occurrence of intrinsic cardiac activity; and hysteresis means for extending said escape interval to an extended duration upon the occurrence of intrinsic cardiac activity, and for returning said escape interval to its normal duration upon the generation of a stimulation pulse.

10. The implantable rate-responsive pacemaker, as set forth in claim 9, further including scan means for selectively increasing said escape interval an incremental amount after each stimulation pulse.

11. The implantable rate-responsive pacemaker, as set forth in claim 9, wherein said hysteresis means further includes hysteresis rate adjust (HRA) means for gradually returning said escape interval to its normal duration over a series of paced cardiac cycles, a paced cardiac cycle comprising a cycle that commences with a first stimulation pulse and concludes with the timing-out of the escape interval immediately following said first stimulation pulse.

12. An implantable dual-chamber pacemaker comprising:

sensing means for sensing intrinsic cardiac activity in a first heart chamber;

pulse generator means for generating a pacing pulse and delivering said pacing pulse to a second heart chamber a prescribed time delay after sensing intrinsic cardiac activity in the first heart chamber, whereby pacing pulses may be delivered to said second heart chamber that track intrinsic cardiac activity, if any, sensed in said first heart chamber;

timing means for generating an escape interval having a normal duration determined by a programmed rate, said normal escape interval plus said prescribed time delay defining the maximum time that may elapse between pacing pulses delivered by said pacing means to said second heart chamber;

said prescribed time delay being initiated upon the sensing of intrinsic cardiac activity in said first heart chamber or the timing-out of said escape interval, whichever occurs first; and hysteresis means for extending said escape interval to an extended duration upon the sensing of intrinsic cardiac activity in said first heart chamber, and returning said escape interval to its normal duration upon the timing-out of said extended duration escape interval without having sensed any intrinsic cardiac activity.

13. The implantable dual-chamber pacemaker, as set forth in claim 12, wherein the timing means generates a present escape interval followed by a next escape interval the dual-chamber pacemaker further including scan means for increasing the next escape interval a prescribed increment upon the timing-out of the present escape interval without having sensed intrinsic cardiac activity in the first heart chamber.

14. The implantable dual-chamber pacemaker, as set forth in claim 12, further including hysteresis adjust means for decreasing the escape interval when extended from its normal duration by a prescribed increment upon the timing-out of the escape interval without having sensed intrinsic cardiac activity in the first heart chamber.

15. A method of adjusting the escape interval (EI) of a rate-responsive (RR) pacemaker so that intrinsic cardiac activity may occur at a slower rate than paced cardiac activity, said RR pacemaker including means for sensing a physiological parameter; timing means for establishing a base escape interval $EI_0$ having a duration that varies as a function of said sensed physiological parameter or a programmed rate, whichever is shorter; said method comprising the steps of:

(a) starting the timing-out of the escape interval $EI_0$;

(b) determining whether intrinsic cardiac activity occurs before the timing-out of the escape interval $EI_0$;

(c) generating a stimulation pulse in the event no intrinsic cardiac activity occurs as determined in step (b) and repeating steps (a) and (b); and (d) initiating a hysteresis mode in the event intrinsic cardiac activity occurs as determined in step (b), said hysteresis mode extending the escape interval $EI_0$ to a hysteresis escape interval, thereby affording a longer period of time for intrinsic activity to occur before a stimulation pulse is generated.

16. The method, as set forth in claim 15, wherein the initiating of said hysteresis mode in step (d) includes:
   (d1) increasing the escape interval to a new value, $EI_H$, where $EI_H = EI_0 + H$, and H is a programmable value or factor derived from $EI_0$ in accordance with a prescribed relationship;
   (d2) starting the timing-out of the escape interval $EI_H$;
   (d3) determining whether intrinsic cardiac activity occurs before the timing-out of the escape interval $EI_H$;
   (d4) repeating steps (d2) and (d3) upon the occurrence of intrinsic cardiac activity as determined in step (d3); and
   (d5) generating a stimulation pulse upon the timing-out of the escape interval $EI_H$ without the occurrence of intrinsic cardiac activity as determined in step (d3), resetting the escape interval to $EI_0$, and returning to step (a).

17. The method, as set forth in claim 16, wherein step (c) further includes initiating a scan mode after the generation of a stimulation pulse, said scan mode causing the escape interval $EI_0$ to be incrementally extended.

18. The method, as set forth in claim 17, wherein the initiating of said scan mode includes:
   (c1) increasing the escape interval to a new value, $EI_S$, where $EI_S = EI_0 + S$, and S is a programmable parameter;
   (c2) determining whether $EI_S$ is equal to $EI_H$, and if so initiating the hysteresis mode as set forth in step (d);
   (c3) in the event $EI_S$ is less than $EI_H$, starting the timing-out of the escape interval $EI_S$;
   (c4) determining whether intrinsic cardiac activity occurs before the timing-out of the escape interval $EI_S$;
   (c5) generating a stimulation pulse upon the timing-out of the escape interval $EI_S$ without the occurrence of intrinsic cardiac activity as determined in step (c4), increasing the escape interval again by the value S so that $EI_S(\text{new value}) = EI_S(\text{prior value}) + S$, and returning to step (c2); and
   (c6) initiating the hysteresis mode as set forth in step (d) upon the occurrence of intrinsic cardiac activity as determined in step (c4).

19. The method, as set forth in claim 16, wherein step (d5) further includes initiating a hysteresis rate adjust (HRA) mode after the generation of a stimulation pulse, said HRA mode causing the escape interval $EI_H$ to be incrementally decreased back to the base escape interval $EI_0$.

20. The method, as set forth in claim 19, wherein the step of initiating the HRA mode includes:
   (d5$_1$) decreasing the escape interval to a new value, $EI_A$, where $EI_A = EI_H - A$, and A is a programmable parameter;
   (d5$_2$) starting the timing-out of the escape interval $EI_A$;
   (d5$_3$) determining whether intrinsic cardiac activity occurs before the timing-out of the escape interval $EI_A$;
   (d5$_4$) in the event intrinsic cardiac activity occurs as determined in step (d5$_3$), repeating steps (d5$_2$) and (d5$_3$);
   (d5$_5$) in the event the escape interval $EI_A$ times-out without the occurrence of intrinsic cardiac activity as determined in step (d5$_3$), initiating the hysteresis mode as previously described;
   generating a stimulation pulse; and
   determining if $EI_A$ has been decreased to $EI_0$, and if so returning to step (a), and if not decreasing the escape interval again by the value A so that $EI_A(\text{new value}) = EI_A(\text{prior value}) - A$, and returning to step (d5$_2$).

* * * * *